United States Patent
Rolland et al.

(10) Patent No.: US 9,492,489 B2
(45) Date of Patent: Nov. 15, 2016

(54) USES OF HIBISCUS, IN PARTICULAR PHARMACEUTICAL USES

(75) Inventors: Yohan Rolland, Macon (FR); Charles Duval, Charnay les Macon (FR)

(73) Assignee: NATUREX, Avignon (FR)

(*) Notice: Subject to any disclaimer, the term of this patent is extended or adjusted under 35 U.S.C. 154(b) by 1020 days.

(21) Appl. No.: 12/599,390

(22) PCT Filed: May 6, 2008

(86) PCT No.: PCT/FR2008/050797
§ 371 (c)(1),
(2), (4) Date: Aug. 27, 2010

(87) PCT Pub. No.: WO2008/148995
PCT Pub. Date: Dec. 11, 2008

(65) Prior Publication Data
US 2010/0323046 A1 Dec. 23, 2010

(30) Foreign Application Priority Data
May 7, 2007 (FR) .................................. 07 54905

(51) Int. Cl.
| | | |
|---|---|---|
| *A61K 36/185* | (2006.01) | |
| *A61K 31/35* | (2006.01) | |
| *A23L 2/39* | (2006.01) | |
| *A23L 2/52* | (2006.01) | |

(52) U.S. Cl.
CPC ............. *A61K 36/185* (2013.01); *A23L 2/39* (2013.01); *A23L 2/52* (2013.01); *A23L 33/11* (2016.08)

(58) Field of Classification Search
None
See application file for complete search history.

(56) References Cited

U.S. PATENT DOCUMENTS

| | | |
|---|---|---|
| 2002/0055471 A1 | 5/2002 | Bailey et al. |
| 2005/0202103 A1 | 9/2005 | Rajendran et al. |

OTHER PUBLICATIONS

Fouda, et al. (2007) Can. J. Physiol. Pharmacol. 85: pp. 1020-1031.*
Roberts (1999) Pathophysiology of Bacterial Cystitis. In: Advances in Bladder Research pp. 325-338.*
Moura et al. (2008) J. Applied Microbiology 106: pp. 1779-1791.*
Wiles et al. (2008) Experimental and Molecular Biology 85: pp. 11-19.*
Alshami et al. (2014) Asian Pac J. Trop. Dis. 4(4): 317-322.*
Website document entitled: "UT Synergy" by David Brody. Available at http://catalog.designsforhealth.com/core/media/media.nl/id.3848/c.ACCT14095/.f?h=244d3810e8d201748d11. Downloaded from website Jun. 18, 2015.*
Website document entitled: "UTIRose: A natural answer to Urinary Tract Infections issues". Available at http://www.pkdiet.com/pdf/herb/HibiscusUTI.pdf. Downloaded from website Jun. 18, 2015.*
International Search Report.
Chuang Chien-Hui et al: "Investigation of the effect of drinking roselle tea on the urine pH and blood pressure of long term foley-installed elderly", Journal of the Chinese Society for Horticultural Science, vol. 50,No. 1, (Mar. 2004), pp. 117-124.
Chang Yun-Ching et al: "Hibiscus anthocyanins rich extract-induced apoptotic cell death in human promyelocytic leukemia cells" Toxicology and Applied Pharmacology, vol. 205, No. 3, (Jun. 2005), pp. 201-212.
Ali Badreldin H et al: "Phytochemical, pharmacological and toxicological aspects of Hibiscus sabdariffa L.: A review" Phytotherapy Research, vol. 19,No. 5, (May 2005), pp. 369-375.

* cited by examiner

*Primary Examiner* — Chris R Tate
*Assistant Examiner* — Russell Fiebig
(74) *Attorney, Agent, or Firm* — Stephen J. Weyer, Esq.; Stites & Harbison, PLLLC.

(57) ABSTRACT

The invention relates to the use of *hibiscus* or of a crude or purified *hibiscus* extract in the preparation of a medicament for the treatment or prevention of urinary infections associated with the presence of *Escherichia coli* and *Candida albicans*, especially for the treatment or prevention of cystitis.

15 Claims, No Drawings

USES OF HIBISCUS, IN PARTICULAR PHARMACEUTICAL USES

The present invention relates to novel uses of *hibiscus*, especially in the pharmaceutical field.

*Hibiscus* (*Hibiscus sabdariffa*) is a plant which is widely grown in West Africa, where it is consumed in the form of a hot or cold drink: karkade.

*Hibiscus* petals contain polyphenols of the flavonol and flavanol type in simple or polymerized form. Among those polyphenols there are found catechin derivatives in monomeric or dimeric form (procyanidin A or B) and flavonoids. *Hibiscus* especially contains a particular flavonoid, gossypetin (3,5,7,8,3',4'-hexahydroxy-flavone), and its glycosylated form, gossypin. That flavonoid has exhibited antibacterial properties in vitro on some microorganisms (Mounnissamy V M; Kavimani S; Gunasegaran R. Antibacterial activity of gossypetin isolated from *hibiscus sabdariffa*. The Antiseptic. 2002 March; 99(3): 81-2), namely *Escherichia coli*, *Staphylococcus aureus*, *Bacillus subtilis*, *Bacillus pumpilus* and *Pseudomonas aeruginosa*.

Epidemiological studies show that more than one in two women will be faced with urinary infections during her lifetime. The microorganism from which such an infection originates is almost always a colibacillus, which naturally colonizes the large intestine in numbers close to billions. Women are far more frequently affected by such an infection than men owing to the anatomical differences in the urinary system: the woman's urethra, which is shorter, facilitates contamination of the bladder by bacteria. Young men are rarely affected by this disorder. However, middle-aged men with prostate trouble are more at risk.

Cystitis, or lower urinary tract infection, is an inflammation of the urinary system caused by proliferation of microorganisms of the type *Escherichia coli*, *Proteus mirabilis*, *Staphylococcus saprophyticus*, etc.

This pathology is in most cases treated with antibiotics. If the infection is of low intensity, it disappears quickly with good hygiene; in the opposite case, antibiotic treatment is necessary. However, it is necessary at all costs to avoid frequent recurrences owing to the development of resistance to the medicaments and especially owing to possible renal complications.

The object of the present invention is to provide a product which allows urinary comfort to be regained.

It is also an object of the present invention to provide a novel medicament for the treatment of urinary disorders and more particularly of cystitis.

The present invention relates to the use of *hibiscus* or of a crude or purified *hibiscus* extract in the preparation of a medicament for the treatment or prevention of urinary infections and more particularly of cystitis.

The prevention and treatment of urinary infections is understood as meaning limiting the frequency with which the urinary infections occur and promoting the disappearance of the pathology.

The urinary infections mentioned here are associated with proliferation of a certain pathogenic flora, resulting in local inflammation of the urinary tract. More particularly, they are associated with proliferation especially of *Escherichia coli* and *Candida albicans*.

The expression "urinary infection" denotes a pathology associated with the abnormal presence of microbial germs in the urine.

More particularly, the present invention relates to the use of *hibiscus* or of a crude or purified *hibiscus* extract in the preparation of a medicament for the treatment or prevention of cystitis.

The term "cystitis" denotes a chronic or acute inflammation, of infectious origin, of the bladder. This specific urinary infection is therefore limited to the bladder (Bergogne-Bézerin E. et al., Les infections urinaires, questions d'actualité. Ed Phase 5, 2002).

A distinction is made between acute uncomplicated cystitis and complicated cystitis.

Acute uncomplicated cystitis affects women less than 65 years old who are not pregnant, not diabetic, without particular urological antecedents and without immunodepression. Repeated acute uncomplicated cystitis occurs up to 4 times per year. Cystitis is recurrent when it occurs more than four times per year.

Complicated cystitis occurs in a particular situation including risk factors (male, pregnancy, diabetes, immunodepression, uronephrological pathology, etc.).

*Escherichia coli* is the bacterium responsible for 80 to 90% of the cases of complicated or uncomplicated urinary infections in France, and especially of acute uncomplicated cystitis. The other bacteria involved in the remaining 10 to 20% of cases have only a low prevalence individually.

In the majority of the other European countries, the prevalence of the microorganisms involved in acute uncomplicated cystitis is similar to that found in France. The prevalence of *E. coli* strains is substantially higher (88%) in the northern countries such as the Scandinavian countries and Poland. In complicated urinary infections, the proportion of species involved is significantly different, *E. coli* strains being less often involved, in favour of *P. mirabilis*, other enterobacteria or enterococci. Accordingly, in a recent study (Hryniewick K. et al., Antibiotic susceptibility of bacterial strains isolated from urinary tract infection in Poland. J Antimicrob Chemother 2001; 47: 773-80), conducted simultaneously in the two types of infection, the prevalence of *E. coli* was 88% in acute uncomplicated cystitis as compared with 66% in complicated urinary infections.

*Candida albicans* is the main yeast responsible for urinary infections such as cystitis. Candiduria follows or coexists with bacteriuria. In a large multicentre study, *C. albicans* represents 52% of the yeasts isolated in cases of cystitis. *C. albicans* is the species that is most frequently found.

The prevalence of the main microorganisms (bacteria and/or yeasts) responsible for urinary infections varies according to the type of infection under consideration.

For example, the spectrum of uropathogenic agents causing complicated cystitis is broader than that of the agents responsible for uncomplicated cystitis.

Consequently, a compound that is effective in treating some urinary infections will not necessarily have the same degree of effectiveness on a more specific infection of the acute uncomplicated cystitis type.

In the case of cystitis (acute uncomplicated), treatment must be directed specifically against the microorganisms that are mainly responsible (specific mechanisms of adhesion, different sensitivity of the strains to the active molecules).

Accordingly, the following germs *E. coli* (bacterium) and *C. albicans* (yeast) are specifically responsible for cystitis, especially acute uncomplicated cystitis.

The present invention is based on the finding that *hibiscus* or *hibiscus* extracts are effective on the 2 main microorganisms responsible for cystitis, owing to their specific antimicrobial action.

*Hibiscus*, in particular the petals, contains a number of organic acids especially of the type AHA (alpha-hydroxy acid). Such acids enable the pH of the urine to be kept acidic and therefore the proliferation of bacteria in the urinary tract to be controlled.

Accordingly, within the scope of the present invention, the use of *hibiscus* or of a crude or purified *hibiscus* extract enables urine to be kept at a pH less than 7, preferably less than or equal to 6, and especially at a pH from approximately 5 to approximately 6, yet more preferably from approximately 5.5 to approximately 6.

*Hibiscus* or a crude or purified *hibiscus* extract can be used in order to regain urinary comfort. Maintaining the pH of the urine at a value less than 7 makes it possible to create a medium that does not promote the development of bacteria.

Advantageously, *hibiscus* or the crude or purified *hibiscus* extract allows the urine to be enriched with polyphenols that are specific to *hibiscus*, such polyphenols having antimicrobial activity and being especially anthocyans or proanthocyanidins.

The chemical composition of *hibiscus* is rich in organic acids, in anthocyans, in polyphenols of the type proanthocyanidins and antibacterial flavonoids. Among the anthocyans present in *hibiscus*, the following may be mentioned: delphinidin-3-O-sambubioside, delphinidin-3-O-glucoside, cyanidin-3-O-sambubioside and cyanidin-3-O-glucoside. Among the flavonoids there may be mentioned gossypetin and its glycosylated form, gossypin, as mentioned hereinbefore.

The present invention relates also to the use as defined hereinbefore in which the *hibiscus* or the crude or purified *hibiscus* extract is in the form of a food supplement.

Such a food supplement can especially be in the form of gelatin capsules, tablets, capsules, soluble powders (sachets or sticks) or drinks (in concentrate form or ready to drink).

The food supplement can therefore be used, for example, by women who wish to regain urinary comfort. It can also be used to prevent urinary trouble and the recurrence thereof.

An advantageous use according to the present invention is characterized in that the *hibiscus* comes from the entire plant, in fresh or dry form, or comes from the flowers.

Within the scope of the present invention, therefore, the *hibiscus* can be used in fresh or dry form, whatever its particle size. Accordingly, the *hibiscus* can be used, for example, in (cryo)ground or micronized form.

Another advantageous use according to the present invention is characterized in that the crude or purified *hibiscus* extract is an extract in liquid form, whatever the solvent (for example an alcohol, water or an aqueous alcoholic mixture), or in dry form, whatever the drying means (especially by removal of water in a stream of hot air, by atomization, by evaporation, by sublimation, by dehydration, or by adsorption on a support).

The *hibiscus* extracts can be crude or purified, obtained by the conventional means of the person skilled in the art.

The crude extract is obtained by placing the plant (*hibiscus*) in the presence of a solvent, such as water, for an extraction step, and separating the plant and the solvent in order to obtain a crude extract in liquid form. In order to obtain a crude extract in dry form, the crude extract in liquid form is dried, for example by removing water in a stream of hot air, by atomization, by evaporation, by sublimation, by dehydration, or by adsorption on a support.

The purified extract is obtained from the crude extract obtained in the preceding step in order to increase the content of active ingredient. To that end, said crude extract is subjected to a purification step either by chromatography or by liquid/liquid extraction with a water-immiscible organic solvent.

Accordingly, starting from a crude extract in liquid form in aqueous phase, obtained either by crude extraction of the plant with water or by crude extraction with alcohol and removal of the solvent, or by redissolution of the crude extract in powder form in water, a purification method by a chromatography technique can be applied.

The crude extract is deposited on chromatography resins. The desired active ingredients (polyphenols) remain fixed to the resin, which is then washed with water or with a water/organic solvent mixture which does not redissolve the desired active ingredients. Finally, the active ingredients are recovered from the column by elution with an organic solvent, for example of the alcohol (e.g. methanol or ethanol) or ketone type. This process allows more than 90% of the active ingredients present in the aqueous starting phase to be recovered.

The purified extracts can be handled in an identical manner in liquid form in an alcohol phase, or in liquid form in an aqueous phase after removal of the solvent, or in liquid form in a concentrated aqueous phase or in dried form (powder form).

The chromatography resins used can be, for example, of the ion (anions or cations) exchange type or of the adsorption/desorption type, for example of the divinylbenzene/styrene copolymer, polystyrene or polymethacrylic type, marketed especially by Rohm & Haas or Mitsubishi Chemical.

The present invention relates also to a medicament comprising *hibiscus* or a crude or purified *hibiscus* extract for the treatment or prevention of urinary disorders, and more particularly for the treatment or prevention of cystitis.

The present invention relates also to a concentrated *hibiscus* extract, in liquid or dry form, having a content of polyphenols greater than or equal to 50%, preferably from approximately 50% to approximately 100%, yet more preferably from approximately 90% to approximately 100%.

More particularly, the concentrated extract according to the invention contains at least 90% total polyphenols, and more particularly from approximately 20 to approximately 50% catechins.

The polyphenols are analyzed by HPLC using as eluant a gradient of the solvents A: water/acetic acid (99/1), B: water/acetic acid (94/6) and C: water/acetonitrile/acetic acid (65/30/5). The applied gradient is as follows:

| Time (min) | % A | % B | % C |
|---|---|---|---|
| 0 | 100 | 0 | 0 |
| 15 | 0 | 100 | 0 |
| 30 | 0 | 100 | 0 |
| 50 | 0 | 90 | 10 |
| 60 | 0 | 80 | 20 |
| 80 | 0 | 70 | 30 |
| 120 | 0 | 0 | 100 |
| 122 | 100 | 0 | 0 |
| 140 | 100 | 0 | 0 |

The applied flow rate is 0.5 ml/min (UV detector: 280 nm; column: C18 grafted phase).

Among the polyphenols, mention may be made of the flavanols and flavonoids on the one hand and the flavones on the other hand.

Among the flavanols and flavonoids there may be mentioned especially the following compounds: hibiscetin, hibiscetrin (hibiscetin-3-0-glucoside), gossypetin, gossypitrin (gossypetin-7-0-glucoside), gossypin (gossypetin-8-0-glucoside), gossytrin (gossypetin-3-0-glucoside), sabdaritrin and its hydrolyzed form sabdaretin (hydroxyflavone), quercetin or myricetin.

Among the flavones there may be mentioned especially the following compounds: luteolin or luteolin glycoside.

According to a particular embodiment, the concentrated *hibiscus* extract according to the invention has an anthocyan content of less than 8%.

The concentrated *hibiscus* extract of the invention is preferably characterized in that it has an anthocyan content greater than or equal to 8%, preferably from approximately 10% to approximately 20% and yet more preferably from approximately 15% to approximately 20%.

The anthocyans are analyzed by HPLC using as eluant a gradient of the solvents B: 3% phosphoric acid (v/v) in Ultrapure water (Millipore) and C: methanol. The applied gradient is as follows:

| Time (min) | B (%) | C (%) |
| --- | --- | --- |
| 0 | 77 | 23 |
| 35 | 74 | 26 |
| 70 | 60 | 40 |

The applied flow rate is 1.0 ml/min (detection: 525 nm; column: C18 grafted phase).

More particularly, the concentrated *hibiscus* extract of the invention is characterized in that it has an anthocyan content with the following distribution:

| | |
| --- | --- |
| delphinidin-3-O-sambudioside (hibiscin) | 4-6% |
| delphinidin-3-O-glucoside | 0-2% |
| cyanidin-3-O-sambudioside (gossypicyanin) | 0-4% |
| cyanidin-3-O-glucoside | 0-1% |

In addition, the concentrated *hibiscus* extract of the invention is characterized in that it has an organic acid content of less than or equal to 30%.

More particularly, the concentrated *hibiscus* extract of the invention can comprise chlorogenic acid in an amount greater than 1% and quinic acid in an amount less than 5%.

Among the organic acids there may also be mentioned the following compounds: protocatechuic acid, citric acid, malic acid, tartaric acid, hibiscic acid or ascorbic acid.

The present invention relates also to a pharmaceutical composition comprising as active ingredient a concentrated *hibiscus* extract as defined above in association with a pharmaceutically acceptable carrier.

The present invention relates also to a food supplement comprising a concentrated *hibiscus* extract as defined above in association with an acceptable carrier.

EXAMPLES

1) Preparation of *Hibiscus* Extracts a) Preparation of a Crude *Hibiscus* Extract:

1 kg of dried *hibiscus* flowers are extracted by maceration in water at 50° C. for 2 hours.

The loaded solvent is separated from the solid material in suspension, filtered and then concentrated.

The concentrate constitutes a liquid crude extract, which can be converted into a crude extract in powder form by removing the solvent, for example by drying in vacuo.

The mass yield is of the order of 30 to 40% w/w.

Analysis of the product shows the presence of organic acids, polyphenols of the proanthocyanidin type, flavonoids and anthocyans.

The analyses show that the extract has a content of more than 20% proanthocyanidins.

b) Preparation of Another Crude *Hibiscus* Extract:

1 kg of fresh *hibiscus* flowers are extracted by maceration in 90% ethanol for 2 hours.

The loaded solvent is separated from the solid material in suspension and then filtered.

The product constitutes a liquid crude extract in which all the desired compounds are likewise found, but with a different distribution.

The liquid product can be distilled and then concentrated and optionally dried by conventional means, for example in vacuo with heat action.

c) Preparation of a Purified *Hibiscus* Extract:

1 kg of dried *hibiscus* flowers are extracted by maceration in 90% ethanol for 2 hours.

The loaded solvent is separated from the solid material in suspension, filtered and then distilled and concentrated.

The concentrate is subjected to a step of purification by chromatography on adsorption/desorption resin suitable for polyphenols.

The eluate then constitutes the purified extract, which can likewise be stored in liquid or dried form.

A purified *hibiscus* extract containing up to 9% anthocyans and up to 50% polyphenols, measured by HPLC, is obtained.

d) Preparation of Another Purified *Hibiscus* Extract:

Starting from a crude extract obtained, for example, as above (paragraph a)), especially in concentrated form, it is possible to apply a step of purification by liquid/liquid extraction with the aid of a water-immiscible solvent, for example of the n-butanol or ethyl acetate type.

The solvent is then removed from the purified fraction, which contains up to 65% polyphenols.

Analyses show that the extract has a proanthocyanidin content of more than 50%.

In all the cases of *hibiscus* extracts in liquid form, it is possible to stabilize the extracts with additives of the glycerol or glycol type, of the preservative type, or with any other formulation ingredient.

2) Examples of Galenical Formulations a) Preparation of a Ready-to-Drink Drink:

| | % |
| --- | --- |
| Water | qs |
| *Hibiscus* extracts | 1 |
| Sour cherry extracts | 1 |
| Meadowsweet extracts | 1 |
| Green tea extracts | 1 |
| Acidity corrector (citric acid) | 2 |
| Natural lime flavouring | 0.2 |

*Hibiscus* allows the appearance of a pathogenic bacterial flora in the urinary tract to be controlled; the other extracts promote the removal of water by increasing diuresis, which contributes to the general positive effect of the drink against infectious pathologies of the urinary tract.

b) Preparation of a Gelatin Capsule:

| | |
|---|---|
| Crude *hibiscus* extract | 210 mg |
| Microcrystalline cellulose | 25 mg |
| Magnesium stearate | 20 mg |
| Silicon dioxide | 10 mg |
| Total | 265 mg |

This type of galenical formulation allows the 36 mg of proanthocyanidins per day proposed by the AFSSA to be provided without difficulty.

3) Microbiological Results

Microbiological studies were carried out in order to show the efficacy of the *hibiscus* extracts of the invention (purified or unpurified) on urinary infections and more particularly on cystitis, especially acute uncomplicated cystitis.
Study No. 1—Evaluation of the Efficacy of the Antimicrobial Preservation of a *Hibiscus* Extract (UtiRose)—Protocol US Pharmacopoeia XXV—2 Strains—7 Days
The aim of this first study is to evaluate the working life of a preservative system in order to ensure that the preservative activity does not change during the preservation period.
The strains used are *Escherichia coli* and *Candida albicans*.
The culture media are new-generation culture media (preservative media, strain maintenance media, validated incubation and counting media) as mentioned below:
Preservative media:
Brain/heart broth
LT 100 broth
Tryptone salt solution
Strain maintenance media:
LT 100 gelose
Trypto-casein soya gelose
Sabouraud gelose
Incubation and counting media (in Petri dishes):
on LT 100 gelose for bacterial strains
on Sabouraud gelose for fungi and yeasts
A control of each batch of medium used for carrying out this test is incubated for 5 days at 32° C. in order to check its sterility.
Method:
The product to be analyzed is artificially contaminated with suitable microorganisms. Between each measurement, the inoculated preparations are kept at 22° C. and with the exclusion of light for 28 days.
Four post-inoculation counts are carried out at 7 days, 14 days, 21 days and 28 days (count of the contaminating flora carried out by successive dilutions of 1 g of product on nutritive gelose).
At each measuring time:
1 g (+/−0.1 g) of contaminated product is weighed in 9 ml of LT 100 broth (+/−0.2 ml)
revivification for 30 minutes, ambient temperature
The product tested is a purified *hibiscus* extract as defined above.
Results in Logarithmic Reduction
Concentrations Measured (UFC/g)

| Strains | Inoculum | d7 |
|---|---|---|
| E. coli | $2.80 \times 10^7$ | $0.00 \times 10^0$ |
| C. albicans | $1.60 \times 10^7$ | $6.30 \times 10^2$ |

Reductions obtained (apart from inoculum)

| Strains | Inoculum | d7 |
|---|---|---|
| E. coli | 7.45 | 7.45 |
| C. albicans | 7.20 | 4.40 |

Interpretation and Conclusion:
The preservative system is effective if:
for bacteria: at d14 there must be a reduction of at least 2 log relative to the starting inoculum. The concentration of microorganisms obtained at d14 must remain identical or lower during the remaining 14 days.
for moulds/yeasts: at d14 and d28 the concentration must be equal to or less than the initial concentration of the inoculum.
The logarithmic reductions comply with the requirements of the Pharmacopoeia in 7 days.
This first study shows that the *hibiscus* extracts according to the invention have a significant efficacy on the reduction of an initial microbial contamination (lowering of the microbial population), both on *E. coli* and on *C. albicans*.
Study No. 2—Evaluation of the Efficacy of the Antimicrobial Preservation of a *Hibiscus* Extract (UtiRose)—Protocol US Pharmacopoeia XXV—1 Strain
The strain used is *Escherichia coli*.
The culture media are identical with those used in study no. 1.
Method:
The product to be analyzed is artificially contaminated with appropriate microorganisms. Between each measurement, the inoculated preparations are kept at 20° C. and with the exclusion of light for 4 days.
Four post-inoculation counts are carried out at 1 day, 2 days, 3 days and 4 days (count of the contaminating flora carried out by successive dilutions of 1 g of product on nutritive gelose).
At each measuring time:
1 g (+/−0.1 g) of contaminated product is weighed in 9 ml of LT 100 broth (+/−0.2 ml)
revivification for 30 minutes, ambient temperature.
The product tested is a purified *hibiscus* extract as defined above.
Results in Logarithmic Reduction
Concentrations Measured (UFC/g)

| Strains | Inoculum | d 1 | d 2 | d 3 | d 4 |
|---|---|---|---|---|---|
| E. coli | $2.80 \times 10^7$ | $3.40 \times 10^2$ | $0.00 \times 10^0$ | $0.00 \times 10^0$ | $0.00 \times 10^0$ |

Reductions Obtained (Apart from Inoculum)

| Strains | Inoculum | d 1 | d 2 | d 3 | d 4 |
|---|---|---|---|---|---|
| E coli | 7.45 | 4.92 | 7.45 | 7.45 | 7.45 |

Interpretation and Conclusion:
The preservative system is effective on the strain tested according to the recommendations of the Pharmacopoeia.
The *hibiscus* extracts demonstrated significant antimicrobial activity on the *E. coli* strains.
The antimicrobial effect on *E. coli* appears immediately and allows total decontamination to be obtained in the 24 hours following the start of treatment: the treatment enabled a reduction of $10^5$ of the initial bacterial population to be obtained within 24 hours.

Study No. 3—Efficacy and Acceptability of a Food Supplement on Urinary Comfort

1—Summary of the Protocol

Aim of the study: to evaluate the efficacy and acceptability of a food ingredient (*hibiscus* extracts as defined above) for improving urinary comfort and preventing urinary infections, taken in the form of a food supplement over a period of 24 weeks by 60 women, distributed in 3 groups, who test either a control product without active ingredient (placebo), or a test product with a dose no. 1 of the ingredient, or another test product with a dose no. 2 of the ingredient.

The products are distributed in neutral packaging coded by the doctor according to the group allocated at random (random distribution in 3 groups of 20 individuals).

The inclusion criteria for the recruitment of volunteers are as follows:
women aged 18 to 55 years
women complaining of urinary discomfort and stating that they have repeated urinary infections.

Dosage: 2 Gelatin Capsules Per Day
Food supplement 1: UtiRose regular (*hibiscus* extract)
Food supplement 2: UtiRose premium (purified *hibiscus* extract)
Control product: maltodextrin.

The test is a controlled, randomized, double blind test. The 3 groups test the products in parallel.

2—Evaluation Criteria

The evaluation parameters are of 2 types: an objective measurement on the one hand, namely the number of occurrences of urinary trouble declared during the test period, and a subjective measurement on the other hand, by evaluation of the perceived efficacy, the acceptability and the tolerance of the products.

The medical examination is carried out by medical visits after 84 and 168 days' consumption of the test products.

Urinary comfort is monitored daily and noted in an observation record, which allows all occurrences of urinary trouble and any declared urinary infections to be recorded.

A questionnaire for evaluating the perceived efficacy is distributed to the volunteers on d4 and d168. It allows the efficacy of the test products on urinary comfort and on the prevention of urinary infections to be evaluated.

Tolerance of the test product is evaluated by the doctor in order to record any undesirable effect associated with consumption of the food supplement.

At the end of the study, the volunteers assessed the ease of use of the products and reported their general impressions through the main qualities and main faults which they perceived in the food supplement.

3—Results

Objective Data

The number of urinary infections fell significantly in the 2 groups which consumed the purified or unpurified active ingredient, whereas it did not fall significantly in the control group.

Autoevaluations

A significant reduction in urinary trouble was noted for the 2 *hibiscus* extracts, in terms of frequency, pain, duration, frequency of micturition, odour of the urine.

A significant improvement in the condition of the mucosa was also observed for the 2 *hibiscus* extracts, in terms of irritation, inflammation, itching, dryness, healthy or unhealthy mucosa.

Subjective Data

The action of the *hibiscus* extracts was considered to be effective by the doctor in preventing urinary infections and the extent of urinary trouble when infection was not present.

In general, the volunteers judged the treatments with *hibiscus* extracts to be satisfactory in the following aspects:
improvement in urinary comfort
respect for the natural microbial flora
effective in preventing urinary trouble and infections
marked reduction in urinary infections
reduction in the intensity of pain during infections
reduction in the duration of urinary infections
reduction in itching and irritation.

The invention claimed is:

1. A method for the treatment or limiting the occurrence of urinary infections associated with the presence of *Escherichia coli* and *Candida albicans*, comprising administering to a subject in need thereof an effective amount of a purified *hibiscus* (*Hibiscus sabdariffa*) extract, wherein the purified extract is prepared by the following steps:
   (a) extracting a *hibiscus* plant by macerating in a solvent for a duration of time and separating the solvent and concentrating to produce a crude extract, and
   (b) purifying the crude extract by subjecting the crude extract to purification by either (1) chromatography on adsorption/desorption resin or (2) liquid/liquid extraction with a water-immiscible organic solvent different from the solvent used to produce the crude extract in step (a), to produce the purified *hibiscus* extract, wherein the purified *hibiscus* extract has reduced organic acid content relative to the crude extract produced in step (a).

2. The method of claim 1, wherein the *hibiscus* extract is in the form of a food supplement.

3. The method of claim 1, wherein the *hibiscus* extract is produced from a whole plant, in fresh or dry form, or from flowers of the plant.

4. The method of claim 1, wherein the *hibiscus* extract is an extract in liquid or dry form.

5. The method of claim 1, wherein the *hibiscus* extract has a polyphenol content greater than or equal to 50% by weight.

6. The method of claim 1, wherein the *hibiscus* extract has an anthocyan content greater than or equal to 8% by weight.

7. The method of claim 1, wherein the *hibiscus* extract is combined with a pharmaceutically acceptable carrier.

8. The method of claim 3, wherein the *hibiscus* extract is produced from flowers of a *hibiscus* plant.

9. The method of claim 1, wherein the *hibiscus* extract comprises at least one flavonoid selected from the group consisting of rutin and quercetin.

10. The method of claim 9, wherein the *hibiscus* extract comprises both rutin and quercetin.

11. The method of claim 1, wherein *hibiscus* extract comprises a measurable amount of ethyl ester.

12. The method of claim 1, wherein the organic acids present in the *hibiscus* extract have been reduced by at least one order of magnitude over the amount of organic acids in its crude extract.

13. The method of claim 1, wherein the *hibiscus* extract is produced from *hibiscus* using organic solvent extraction.

14. The method of claim 13, wherein the organic solvent extraction includes extraction using alcohol.

15. A method for the treatment or limiting the occurrence of cystitis, comprising administering to a subject in need thereof an effective amount of a purified *hibiscus* (*Hibiscus sabdariffa*) extract, wherein the purified extract is prepared by the following steps:

(a) extracting a *hibiscus* plant by macerating in a solvent for a duration of time and separating the solvent and concentrating to produce a crude extract, and
(b) purifying the crude extract by subjecting the crude extract to purification by either (1) chromatography on adsorption/desorption resin or (2) liquid/liquid extraction with a water-immiscible organic solvent different from the solvent used to produce the crude extract is step (a), to produce the purified *hibiscus* extract,
wherein the purified *hibiscus* extract has reduced organic acid content relative to the crude extract produced in step (a).

* * * * *